(12) United States Patent
Ramaseder et al.

(10) Patent No.: US 7,006,216 B2
(45) Date of Patent: Feb. 28, 2006

(54) DEVICE FOR THE CHEMICAL ANALYSIS OF MATERIAL SAMPLES AND METALLURGICAL VESSEL THEREFOR

(75) Inventors: Norbert Ramaseder, Linz (AT); Johannes Heitz, Linz (AT); Johann Gruber, Hohenzell (AT); Dieter Bauerle, Altenberg (AT)

(73) Assignee: Voest-Alpine Industrieanlagenbau GmbH & Co., Linz (AT)

( * ) Notice: Subject to any disclaimer, the term of this patent is extended or adjusted under 35 U.S.C. 154(b) by 0 days.

(21) Appl. No.: 10/395,209

(22) Filed: Mar. 25, 2003

(65) Prior Publication Data

US 2003/0218747 A1 Nov. 27, 2003

Related U.S. Application Data

(63) Continuation of application No. PCT/AT01/00306, filed on Sep. 27, 2001.

(30) Foreign Application Priority Data

Sep. 28, 2000 (AT) .............................. A 1647/2000

(51) Int. Cl.
*G01N 21/63* (2006.01)
(52) U.S. Cl. .................................... 356/318
(58) Field of Classification Search ................. 356/318
See application file for complete search history.

(56) References Cited

U.S. PATENT DOCUMENTS 4,563,567 A    1/1986   Geffroy et al.
4,645,342 A    2/1987   Tanimoto et al.
4,698,483 A   10/1987   Marinoni et al.
4,818,106 A    4/1989   Koch et al.
4,892,992 A    1/1990   Akeel et al.
4,986,658 A    1/1991   Kim
4,995,723 A    2/1991   Carlhoff et al.

FOREIGN PATENT DOCUMENTS

DE    3413589 A1    10/1985
EP    0 362 577 A2   4/1990
JP    5-40092    *   2/1993

(Continued)

OTHER PUBLICATIONS

A. Knight et al., "Characterization of Laser-Induced Breakdown Spectroscopy (LIBS) for Application to Space Exploration", *2000 Society for Applied Spectroscopy*, vol. 54, No. 3, 2000, pp. 331-340.

*Primary Examiner*—F. L. Evans
(74) *Attorney, Agent, or Firm*—Dickstein Shapiro Morin & Oshinsky LLP (57) ABSTRACT

A device for the chemical analysis of solid or molten material samples, based on laser-induced emission spectroscopy, including a laser source generating a laser beam, a deflection device deflecting the laser beam, a focusing device focusing the laser beam, a device that guides the reflections of a plasma ignited by the laser beam on the material sample to an evaluation device. To arrange the laser source and the evaluation device remotely from the material sample, an arm having at least one movable joint and a cavity for the laser beam is provided between the laser source and the material sample for guiding the laser beam. The deflection device is shaped as a mirror or a prism and is provided at the articulation of the arm, whereby the laser source and the evaluation device are arranged to be independent of the material sample in terms of their movements.

22 Claims, 5 Drawing Sheets

FOREIGN PATENT DOCUMENTS

| | | |
|---|---|---|
| JP | 5-40094 | 2/1993 |
| JP | 11-326206 | 11/1999 |
| WO | WO 97/22859 | 6/1997 |
| WO | WO 99/49301 | 9/1999 |

* cited by examiner

DEVICE FOR THE CHEMICAL ANALYSIS OF MATERIAL SAMPLES AND METALLURGICAL VESSEL THEREFOR

This is a continuation of International Application No. PCT/AT01/00306, filed Sep. 27, 2001.

The invention relates to a device for the chemical analysis of solid or molten material samples, in particular of metal melts present in a metallurgical vessel, such as steel melts, based on the laser-induced emission spectroscopy, comprising a laser source generating a laser beam, a deflection device deflecting the laser beam, a focusing device focusing the laser beam as well as a device that guides the reflections of a plasma ignited by the laser beam on the material sample to an evaluation device such as a spectrometer.

In this manner, for instance, the relative amounts of individual elements such as iron, carbon, silicium, manganese, copper, chromium, nickel, aluminium, tin, zinc, vanadium, titanium, sulphur and phosphorus in a solid or liquid material sample, e.g., a metal sample, can be determined. In doing so, a plasma is ignited by a concentrated laser beam on the surface of a material sample, whereby suitably all sensitive parts of the evaluation device, in particular a spectrometer, an evaluation and control computer and the laser source, are to be protected from any influences of the material sample (heat, dust, radioactivity etc.).

Using laser-induced emission spectroscopy for analysing metallic samples is known, for instance, from U.S. Pat. No. 4,645,342 A. According to that document, the analysis system consists of a laser source the beam of which is concentrated on the surface of a steel sample to be analysed where it triggers a plasma break. Typically, tunable laser beams having a pulse length of between 1 fs and 109 ms and a light-wave length of between 120 nm and 20000 nm are used for that. The light scattered by the plasma contains the spectral lines of the elements contained in the sample so that it is feasible to infer the composition of the sample from a spectral analysis of the emitted light with a high degree of accuracy by using a spectrometer.

In U.S. Pat. No. 4,986,658 A, a system for receiving laser-induced emission spectra is described, wherein all components are housed in a cooled casing. Said assembly was chosen such as to be able to also analyse liquid metal samples at high temperatures. However, in doing so the entire detection system and in particular the focusing lenses have to be brought very close to the metal melt so that many fitting positions, e.g. in a nozzle, are ruled out from the beginning because of the large dimensions of said assembly. The small distance must be observed very carefully since the focusing lenses only have very low focusing depths due to the small focal distance. For that purpose, the assembly is equipped with an additional optical distance meter based on the triangulation method.

EP 0 362 577 A illustrates a method for the optical coupling of an analysis system based on the laser-induced emission spectroscopy to a nozzle provided with a window. Thereby, it is achieved that a device for coupling the emitted light into an optical fibre can be installed at the outer surface of a metallurgical vessel and that also the laser can be placed at the outside of the vessel. But also at the outer surface of a metallurgical vessel containing a metal melt, very harsh environmental conditions prevail so that the attached constructions have to be provided with sophisticated protection devices against heat, dust load and slag discharge. Under those conditions, adjusting and maintaining especially the laser source is associated with greater expenditures.

Operating the nozzle such as to cause the emergence of a stable liquid surface to be analysed is difficult since the development of smoke in the nozzle, freezing of the metal melt at the inside nozzle end, strong turbulences of the liquid level and rapid wear of the nozzle may be the result.

WO 97/22859 describes a device for determining the light scattered by a metal melt, allowing the provision of a sufficiently stable liquid metal surface at the end of the nozzle due to a particular geometry of the nozzle and the use of various gases. The analysis of the light scattered by the surface of the liquid permits an exact measurement of the temperature or, in combination with a focused laser beam, a chemical analysis of the melt.

In WO 99/49301, a method for a calibration-free analysis by means of the laser-induced emission spectroscopy is described. In said method, the temperature of the laser-induced plasma is determined by comparing different lines of a single element. By including a large spectral region it is possible to determine the composition of the samples without any comparison to a known reference. However, including the spectra as well as evaluating them is very time-consuming and hence unsuitable for a quick online analysis.

The invention aims at avoiding the above mentioned disadvantages and difficulties and has as its object to provide a device of the initially described kind, which is suitable for the continuous operation of an analysis system based on the laser-induced emission spectroscopy under extremely harsh conditions, in particular those of the metal industry. Thereby, it is desirable to place all sensitive components of the system, i.e. the evaluation device usually comprising a spectrometer, an evaluation and control computer, as well as the laser source as far away from the sample surface as possible, since in this manner the expenditures for protective measures against harsh environmental conditions prevailing during operation and maintenance could be decreased substantially.

According to the state of the art, however, said problem has not been solved for the metallurgical industry since so far it has been impossible in particular to transport the laser light across larger distances in such a manner that it would be feasible to generate a plasma break on the material sample. Similar problems also arise in other potential applications of the laser-induced emission spectroscopy, e.g. when analysing material samples in radioactively charged areas of nuclear reactors or when using said method for space missions. It is true that Knight and his co-authors (A. K. Knight et al., Applied Spectroscopy, 54, 331 (2000) describe a system of receiving laser-induced emission spectra, which system is designed for being incorporated in a future Mars probe and with which it should be possible to analyse samples with the laser beam at a distance of up to 20 m from the last deviation mirror, which, however, presupposes a linear, freely inspectable path between the last mirror and the material sample to be analysed. But just that is not provided in the metallurgical industry because of the pollution of the air by dust and smoke, because of the lack of free spaces and because of the requirement that the aggregates are freely accessible. In addition, it has to be taken into account that metallurgical vessels usually are movable, e.g. tiltable, and are subjected to vibrations and thrusts during operation.

The object underlying the invention is achieved in that, between the laser source and the material sample, an arm equipped with at least one movable joint and having a cavity for the laser beam is provided for guiding the laser beam, with the deflection device shaped as a mirror or a prism being provided at the articulation thereof, and in that the laser source as well as the evaluation unit are arranged so as to be independent of the material sample in terms of their movements.

By the aid of such a device it is feasible to carry out a continuous analysis of samples by means of the laser-induced emission spectroscopy under harsh conditions (with material samples being subjected to thrusts and vibrations) and also with movable sample containers such as converters while keeping a large distance between the sample and the laser source.

According to the mobility required between the material samples and the laser source as well as according to the distance to be bridged over, the arm is equipped with several movable joints and optionally one or several rigid joint(s) and deflection devices shaped as mirrors and/or prisms are provided exclusively at the joints interconnected by arm parts, as well as optionally at the ends of the arm.

A particularly simple construction ensues if the arm is equipped with accessory parts for guiding the reflections to the spectrometer, which accessory parts are also formed by mirrors and/or prisms, whereby advantageously a flexible light-source guide for guiding the reflections to the spectrometer may be provided in addition to or instead of the mirrors and/or prisms.

Such as also to be able to determine the temperature of a sample, the evaluation device is additionally equipped with a pyrometer.

For special applications, the evaluation device suitably is equipped with a device for taking photographic pictures.

The arrangement of the focusing device may be provided either between the joint arranged to be the penultimate one and the joint arranged to be the last one before the material sample or between the last joint before the material sample and the material sample. Such as to adapt to a change in the position of the sample, which may result from, for instance, wear of the fireproof lining of a metallurgical vessel, the focusing device preferably is movable in the longitudinal direction of the laser beam, with the movement of the focusing device suitably being controllable by the reflections.

Such as to be able to take into account a change in the position of the material sample, it also is possible to shape the device such that an arm part arranged between two joints or between a joint and the material sample is telescopically extendable and contractable by means of a movable device in order to keep the distance between the focusing device and the material sample constant.

For a chemical analysis of hot material samples, the arm advantageously is provided with a heat protection, whereby, in addition, the arm also is provided with a cooling device by means of which a cooling medium such as a liquid or a circulation gas such as argon can be conducted through the arm. In this connection, it is advantageous if the arm is equipped with a device for measuring the temperature and a control circuit for minimizing any temperature differences within the arm.

In order to secure optimum mobility of the arm, the laser beam and optionally the reflections are guided so as to be rotationally symmetrical relative to the axis of rotation of the movable joints, in particular by means of the deflection devices shaped as mirrors and/or prisms.

A space-saving construction is characterized in that the deflection devices shaped as mirrors are provided with reflective layers arranged in segments, with one reflective layer being provided for the laser beam and another one for the reflections.

According to a further construction which also is space-saving, the focusing device is equipped with segmented lenses and/or mirrors.

Such as to avoid that a container containing the material sample is burdened by the weight of the arm and such as to balance out any vibrations of the material sample or of a vessel receiving the material sample, respectively, such as a steelworks converter etc., the arm suitably is positioned in space in a moment-free fashion via a weight counterbalance, preferably by means of a counterweight.

A particularly important field of application for the device according to the invention is the metallurgical industry, in particular the ironworks industry. During the determination of the chemical composition of metal melts, shocklike movements of the metallurgical vessel receiving the metal melt occur again and again, as well as dislocations between a fireproof lining of the metallurgical vessel and the outer casing thereof. By means of the construction according to the invention, it is feasible to balance out such shocklike movements and/or vibrations of the metallurgical vessel, which might occur, or possible dislocations of the fireproof lining.

In the metallurgical industry, the invention proves to be particularly advantageous for tiltable metallurgical vessels such as steelworks converters, wherein a part of the arm is arranged in parallel to the tilting axis or—in a manner which does not restrict the mobility and therefore is particularly advantageous—directly in the tilting axis. A steelworks converter comprising a device for determining the chemical analysis of a steel melt is known from the initially described WO-A-97/22859.

In the following, the invention is described in more detail by way of several exemplary embodiments, with reference to the schematic drawing, with FIG. 1 showing the use of the device according to the invention for a steelworks converter illustrated in horizontal section.

FIGS. 2a and 2b illustrate a detail II of

FIG. 1 in vertical section (FIG. 2a) and in a partial view (FIG. 2b).

FIG. 6 shows a detail VI of FIG. 4a, and

Figures 1, 2A:
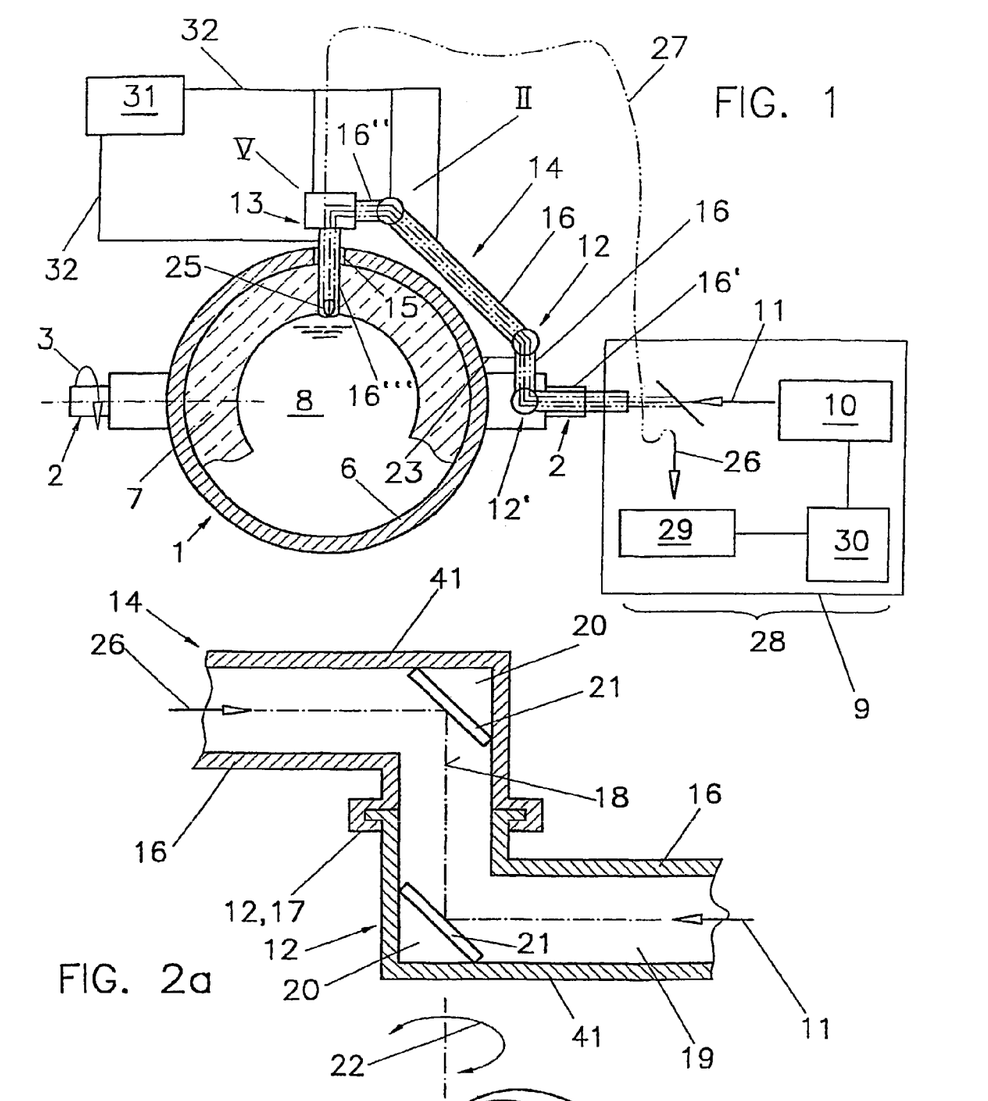

In FIG. 1 a steelworks converter 1 is illustrated in horizontal section, which is pivotable or tiltable, respectively, about its lifting lugs 2 such as indicated by arrow 3. The lifting lugs 2 are arranged in bearings not illustrated further, which are supported on the base or on the converter scaffold 4, respectively, via pillow blocks 5 (cf. FIG. 8). The converter 1 has a steel casing 6 which on its inside is provided with a fireproof lining 7. In the interior of the converter 1, there is a steel melt 8.

Figure 2B:
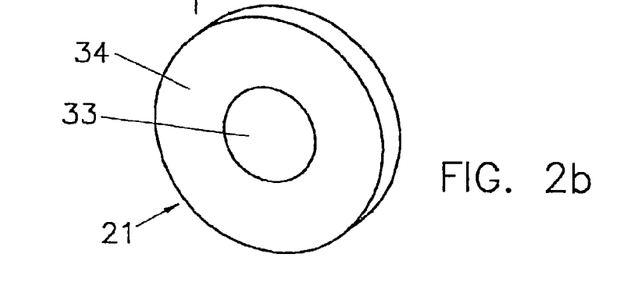

For carrying out a chemical analysis by the aid of the laser-induced emission spectroscopy, a laser source 10 is provided in a protective casing 9 remote from the converter 1. The laser beam 11 generated by the laser source 10 as illustrated by the arrow is guided across an arm 14 equipped with several movable joints 12 and one rigid joint 13 to an opening 15 going through the steel casing 6 of the converter 1 and through the fireproof lining 7 of the same, and further toward the steel melt 8 located in the interior of the converter 1. The movable joints 12 of the arm 14, each connecting two arm parts 16, preferably are shaped such as illustrated in FIG. 2. The arm parts 16 as seen in FIG. 2 are interconnected by a hinge connection 17 in such a manner that they can be pivoted against each other about an axis of rotation 18. The arm 14 has a continuous cavity 19 for the laser beam 11. At the deflection points 20 of the cavity 19, a mirror 21 or a prism for deflecting the laser beam 11 is provided in each case. The capacity of being twisted against each other of the two arm parts 16 connected by a joint 12 is illustrated by a double arrow 22 in FIG. 2.

The mirrors 21 in the joints 12 as illustrated in FIG. 2 each are mounted in pairs, enabling the arm parts 16 to rotate freely about the axis of connection of the two mirrors 21, which is identical with the axis of rotation 18, without thereby changing the properties of the reflected light. By combining several joints 12, each of which is connected by straight stable pipes forming the arm parts 16, a movable arm may be manufactured with a length of 2 m and far more than that.

The mirrors 21 consist of polished metal surfaces (f.i. of polished copper), of metal layers deposited on a substrate (f.i. vacuum-metallized aluminium or silver), which optionally are also provided with a thin protective layer, f.i. made of magnesium fluoride, or of dielectric layer systems also applied onto a substrate.

According to FIG. 1, a first arm part 16' goes through the lifting lug 2. However, it may also be conducted past the same (cf. FIG. 8). An arm part 16 originating from the first joint 12' is fitted to the exterior of the pot by means of a supporting device 23.

The two arm parts 16" and 16''' which are last in the direction of the laser beam are interconnected by a rigid joint 13, whereby the last arm part 16''' passing through the fireproof lining 7 of the converter 1 is ridigly connected with the fireproof lining 7. Such as to allow movements of the fireproof lining 7 relative to the steel casing 6 of the converter 1 without any damage to said last arm part 16''', the opening 15 is designed in the region of the steel casing 6 with a diameter larger than the outside diameter of the last arm part 16'''. Said last arm part 16''' has only a very small inside diameter; suitably ranging between 5 and 50 mm.

Figure 3A:
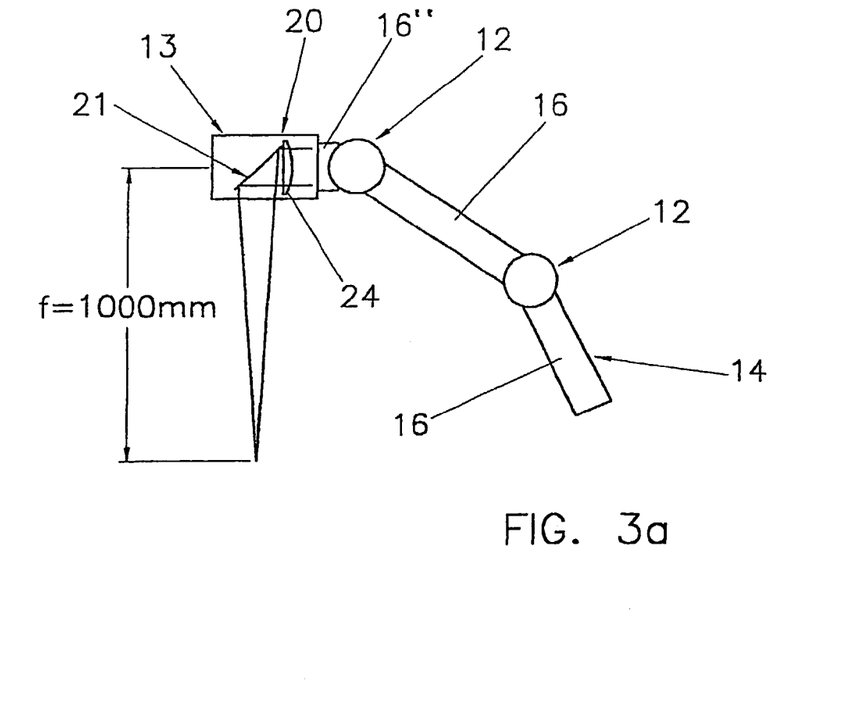
FIGS. 3a and 3b as well as 4a and 4b show details of the device according to the invention in various variants.
Figure 3B:
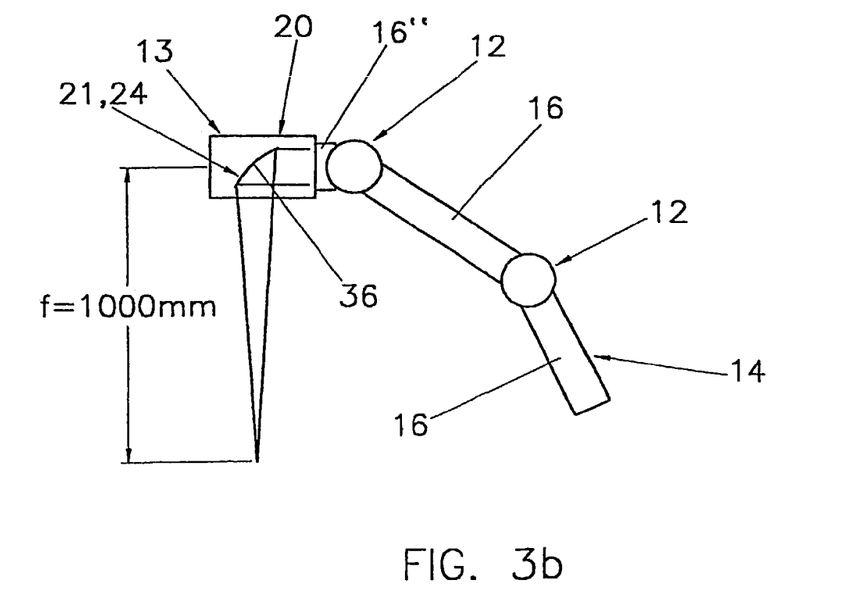
Figure 4A:
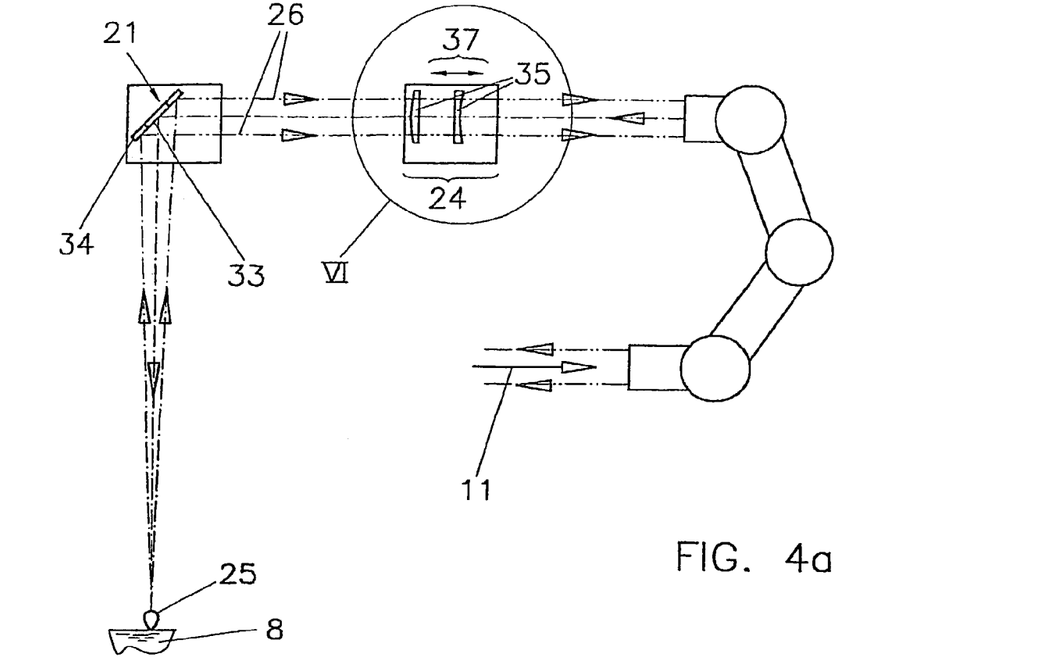

A focusing device 24 is located either in the penultimate or in the last arm part 16", 16'''. Said focusing device 24 may either be designed such as illustrated in FIG. 4a, or it may also be provided in the interior of the rigid joint 13, as seen in FIG. 3, and may be formed by a convex lens or a concave mirror, which at the same time constitutes a deflection device 21.

The narrow end diameter of the cavity of the last arm part 16''' ensures a sufficiently stable surface of the steel melt 8 on which a plasma 25 is ignited by the focused laser beam 11. The light emitted by the plasma 25 as well as another light coming from the surface of the steel melt 8, in the following referred to as reflections 26, is guiding via an optical waveguide 27 to an appropriate evaluation device 28 in accordance with the illustration of FIG. 1. Said evaluation device 28, which is provided with a detection unit 29 and an evaluation computer 30, is also located in the protective casing 9.

A schematically illustrated supply unit 31 serves to admit a flushing and/or cooling agent to the arm 14. It also is equipped with a control system for supplying the arm 14 sufficiently, whereby advantageously a device for measuring the temperature is provided in the arm 14, by the aid of which the regulation of the supply of the arm 14 with flushing and/or cooling agent can be carried out. Preferably on its outside, the arm 14 is equipped with a heat protection, and its cavity 19 is connected to a line 32 originating from the supply unit 31 and admitting a cooling medium, for instance, to a supply line for a flushing gas such as argon. Thereby, the focusing device 24 is also protected against the effects of heat. In the interior of the last arm part 16''' or in the interior of the last rigid joint 13, a window is provided for avoiding that heat is radiated from the interior of the converter 1, which window is incorporated at such an angle to the laser beam 11 that reflection losses are minimized.

By the aid of the evaluation device 28, not only the chemical composition of the steel melt 8 can be determined but also other pieces of information detectable from the reflections 26 can be elicited such as the temperature of the steel melt 8, the temperature of the laser-induced plasma 25, the exact position of the surface of the steel melt 8 as well as also a video image of the surface of the steel melt 8.

According to a particularly advantageous embodiment (cf. FIG. 4a) of the invention, wherein both the laser beam 11 and the reflections 26, i.e. the plasma emission and any other light coming from the sample surface, are guided through a single arm 14, it is required that the mirrors 21 have a sufficiently high reflectivity across the entire necessary spectral region both for the laser beam 11 and for the returned reflections 26, without the mirrors 21 being damaged by the intensive tunable laser radiation 11. In case of full mirrors, that may be achieved either by an appropriate material selection, an appropriate selection of the laser wavelength or of the diameter of the beam. For instance, there are mirror systems having a relatively high reflectivity (in particular Al, Cu, etc.) ranging from medium infrared, across the entire visible range, to far into the ultraviolet range. If a sufficiently large diameter is chosen for the laser beam, said mirrors 21 may also be used in case of high laser capacities, in particular if the mirrors 21 additionally are cooled and the entire arm 14 is flushed with an appropriate protective gas (for example argon).

Another possibility consists in using segmented mirrors such as illustrated in FIG. 2b. Here, an additional device formed by a high-capacity laser mirror 33 is inserted in the centre of each mirror 21, which laser mirror is radially surrounded by a second ring mirror 34 specifically reflecting the reflections. When using a tunable Nd.YAG laser having a wavelength of 1064 nm, which often is used in the laser-induced emission spectroscopy, dielectric high-capacity mirrors specifically adapted to the wavelength of the laser are made use of, for instance. Those are embedded in highly reflective aluminium mirrors equipped with magnesium fluoride layers and exhibiting very high reflectivities, in particular for the ultraviolet range. It is evident that the function of such mirrors 21 does not depend on the exact shape of the mirrors 21. Instead of round mirrors 21, also rectangular or elliptic mirrors 21 and other shapes in arbitrary combinations might be used, for instance. Thereby, it is essential that the diameter of the laser beam 11 has the same or a smaller dimension than the high-capacity mirror 33.

In order to generate a bright plasma 25 on the sample surface by means of the laser beam 11, the laser beam 11 must be concentrated by the aid of a focusing device 24 such as mentioned above. For said concentration, either one or several optical lenses 35 together with plane mirrors 21 or concave mirrors 36 are used (FIG. 3b), possibly also in combination with further plane mirrors 21. In FIGS. 3a and 3b, such devices are schematically illustrated. Thereby, both the plane mirrors 21 and the concave mirrors 36 may be designed as full mirrors or as segmented mirrors. If lenses 35 are used, lens errors must be considered, which might lead to different focal distances at different wavelengths, whereby problems are caused if also the returned light is to be recollected by said lenses 35. In contrast to that, a concave mirror 36 is always free from dispersions. However, achromatic lens systems may be used. In both cases, the typical focal distances, f, of the focusing elements for the example of a steel converter as described in FIG. 1 are provided on the order of about 1000 mm.

In practice, the position of the sample surface often is not fixed but changes in the course of the production process, f.i., in case of a metallurgical vessel (converter 1) by bum-up of the brick-lining material 7. Therefore, an adjustment means 37 (cf. FIG. 6) may be integrated in the focusing device 24 in order to compensate for said change. In FIG. 4*a*, an assembly is exemplified for the case that both the laser beam 11 and the reflections 26 are guided through a single arm 14, and in FIG. 4*b* for the case that the reflections 26 are completely or partially guided across an additional optical waveguide 27.

According to FIG. 4*a*, the laser beam 11 is guided across the arm 14 and is focused onto the material sample 8 by means of a focusing device 24 in order to ignite a laser-induced plasma 25 there. In doing so, the laser beam 11 is additionally deflected by 90°, f.i., around the central part 33 of a segmented mirror 21. In order to compensate for any variations in the distance between the material sample 8 and the last deviation mirror 21 or the lens system 24, respectively, the lens system 24 is mounted on an adjustment unit 37. In addition, an adjustment unit may be integrated in the lens system 24 itself, varying the distance between the individual lenses 35.

The reflections emitted by the plasma 25 or by the material sample 8 itself are also deviated around the segmented mirror 21 and, again with the lens system 24, are guided across the same arm 14 to the evaluation device 28. If the returned signal, i.e. the reflections 16, is detected as a function of the sample distance variable by the adjustment unit 37, the exact distance between the lens system 24 and the material sample 8 may be calculated therefrom.

Figure 4B:
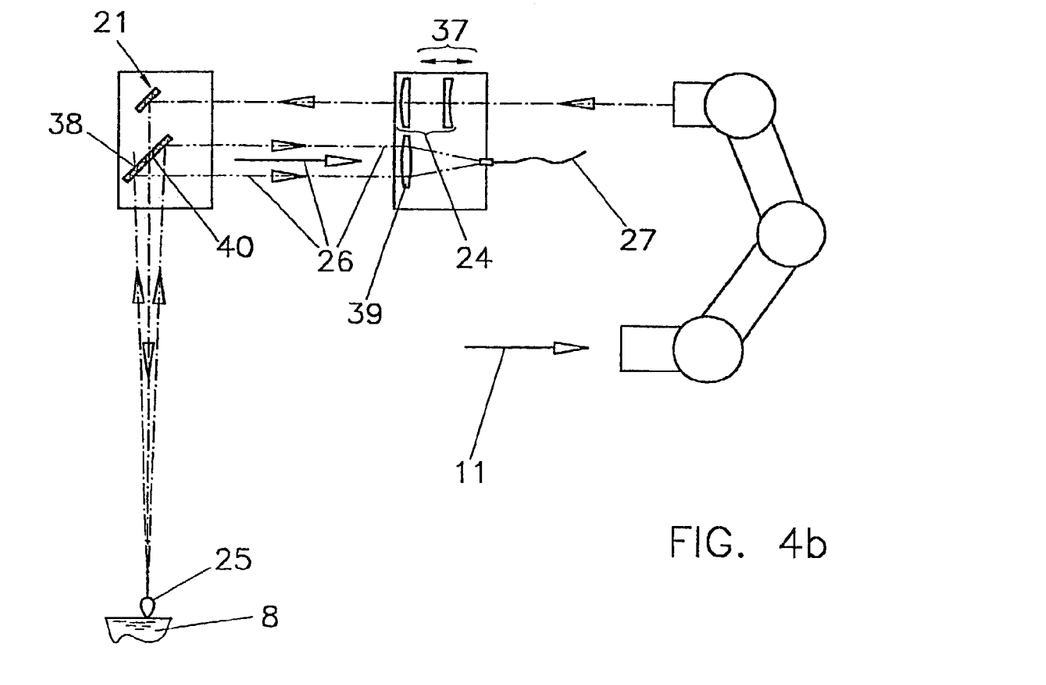

FIG. 4*b* shows a variation of said assembly. Again the laser beam 11 is guided across the arm 14, is focused by means of a focusing device 24 and is deflected to the material sample 8 by the aid of a deviation mirror 21 in order to ignite a plasma 25 there. The reflections 26 emitted by the plasma 25 or by the material sample 8 itself are separated from the course of the laser beam by means of a beam splitter 38 and are deflected and coupled to an optical waveguide 27 via an additional lens 39 fitted to the lens system. Via said optical waveguide, they are then guided to the evaluation device 28. An adjustment unit 37 again permits the variation of the distance between the lens system and the sample.

According to FIG. 4*b*, the beam splitter 38 is realized by a mirror having a hole 40 but may also be comprised of other optical elements, f.i., of partially permeable or wavelength-dependent mirrors. Also in other places, such beam splitters 28 may be used for completely or partially decoupling the reflections 26 from the course of the laser beam 11, such as indicated in FIG. 1. A sequential structure of such arrangements is possible as well in order to evaluate the reflections 26 by means of various evaluation devices 28, fi., one or several spectrometers, a pyrometer and a video camera. In doing so, it is possible that said beam splitters 38 and the evaluation devices 28 are located at different points in the assembly of the device. For example, the laser beam 11 and the infrared light scattered by the material sample 8 might be guided across the arm 14 and the infrared light might be decoupled at the end of the arm 14 and might be sent to a pyrometer for a measurement of the temperature. A portion of the reflections 26 of the laser-induced plasma 25 in the ultraviolet and visible spectral regions is decoupled before the deviation mirror 21 such as in FIG. 4*b* and is guided across a long optical waveguide 27 to a spectrometer for a measurement of the relative amounts f.i. of the elements iron, carbon, silicium and copper contained in the sample, by means of the method of laser-induced emission spectroscopy. Another portion of the reflections emitted by the plasma in the spectral region below 185 nm, which may be transmitted only to a limited extent via a conventional optical waveguide 27, is decoupled still before the entry of the optical waveguide 27. By means of a minispectrometer, adapted to a single wavelength, the sulphur content in the sample is measured. In addition, the visible image of the material sample 8 is recorded with a small video camera which is mounted beside the entry of the optical waveguide 27. It is evident that many other apparent variations of the device according to the invention are possible.

The advantages of the device according to the invention mainly consist in that the laser beam 11 is transported through the arm 14 across a relatively long distance in good quality, i.e. especially exhibiting a mode profile which is almost unchanged and a small divergence. Thereby, it is possible on the one hand to move the laser source 10 away from the industrial metallurgical aggregate 1 in which the material sample 8 to be analysed is located by a sufficiently large distance, hence decisively decreasing the expenditures for protective measures against the harsh environmental conditions, whereas on the other hand it is still possible, owing to the good quality of the beam, to focus the laser beam 11 with sufficiently large focal distances upon its emergence from the arm 14. Only that permits, for example, the operation of the system at an opening 15 in a metallurgical vessel 1 (f.i. steel converter 1). Thereby, the device according to the invention differs from the transmission of laser-light by flexible optical waveguides based, for instance, on glass fibres, whereby the laser light has such a high divergence at the output of the beam that either very small focal distances have to be utilized or unrealistically large lenses or concave mirrors must be used for focusing.

Small focusing areas are required for high intensities of radiation. In addition to that, especially lasers with short pulses having pulse lengths of below one microsecond are used for the method of laser-induced emission spectroscopy in order to avoid segregated evaporation and to be able to temporally filter off the thermal background of the plasma 25. However, for the transmission of beams 11 of a sufficiently high intensity of such short-pulse lasers via glass fibres, a full technological solution still has not been found. In contrast to that, the arm 14 provided according to the invention is equipped with joints 12 interconnected via stable pipes 41. The length of the pipes 41 is limited by the stability of the pipes 41, whereby a length of a few meters does not constitute a problem.

In addition, telescopic elements with variable lengths may be integrated in the arm 14. Such arms 14 may be combined arbitrarily and are easily fabricable as gas- and dustproof embodiments in an industrially suitable version, possibly comprising an additional cooling device. In doing so, arms 14 arbitrarily movable in two or three dimensions may be constructed, and thus the laser beam 11 may also be focused onto almost any point in space. However, it has to be taken into account that any reflection entails losses which grow exponentially with the number of mirrors 21. In the particularly advantageous embodiment of the present invention, both the light of the laser beam 11 and the reflections 26 returned from the material sample 8 to the evaluation device 28 for being analysed are guided across the same arm 14. In doing so, a slight adjustment of the positioning of the laser focus on the material sample 8, fi., by a one-sided heating of the pipe 41 of the last arm part 16 or by vibrations of the arm 14, has virtually no effect on the intensity of the reflections 26, since the evaluation device 28 always monitors the same region of the plasma on the material sample 8 by using the same mirrors 21 in the arm 14. In contrast to that, fluctuations of intensity may occur when returning the reflections 26 separately, if there are variations in the positioning of the laser focus on the material sample 8.

Figure 5:
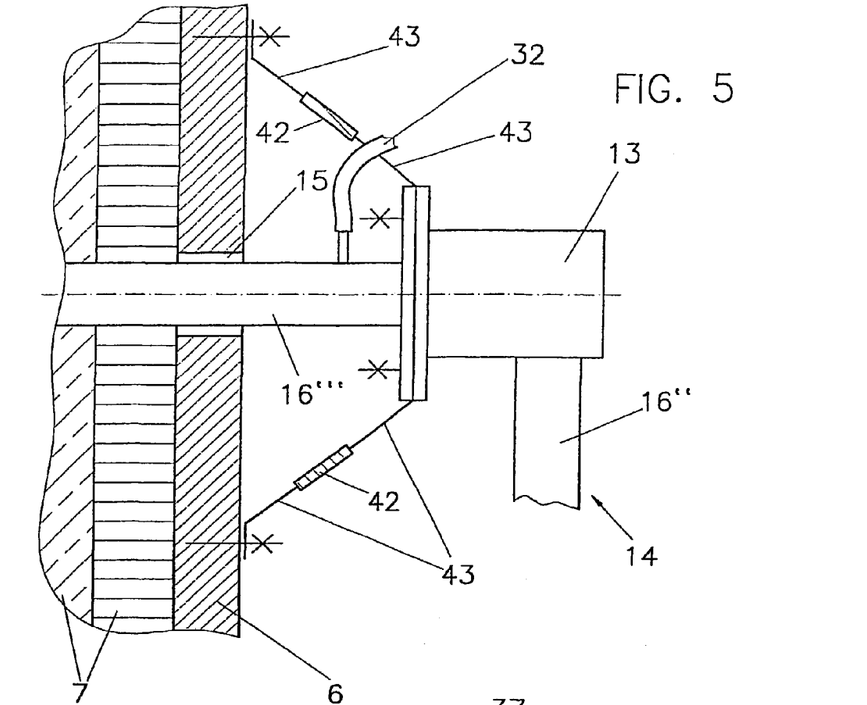
FIG. 5 illustrates a detail V of FIG. 1.

In FIG. 5, the support of the last rigid articulation 13 on a metallurgical vessel 1, i.e. on the metallic outer casing 6 thereof, is illustrated. Due to the embedding of the last arm part 16''' in the fireproof material 7, deformations may occur if said arm part 16''' is burdened by a weight. In order to avoid that, the last articulation 13 rigidly connected to the last arm part 16''' is securely fixed to the metallic outer casing 6 of a metallurgical vessel 1 by means of tension jacks 42 and threaded rods 43. By the aid of the tension jacks 42 suitably extending in three different directions roughly lying on a cone-shaped shell, an exact adjustment of the last joint 13 may be carried out so that the last arm part 16''' projects through the last joint 13 without any weight burden and the arm 14 projects into the interior of the metallurgical vessel 1. By the aid of the tension jacks 42, a readjustment may be carried out at any time, in case there are displacements of the fireproof material 7 relative to the outer casing 6 of the metallurgical vessel 1.

Figure 6:
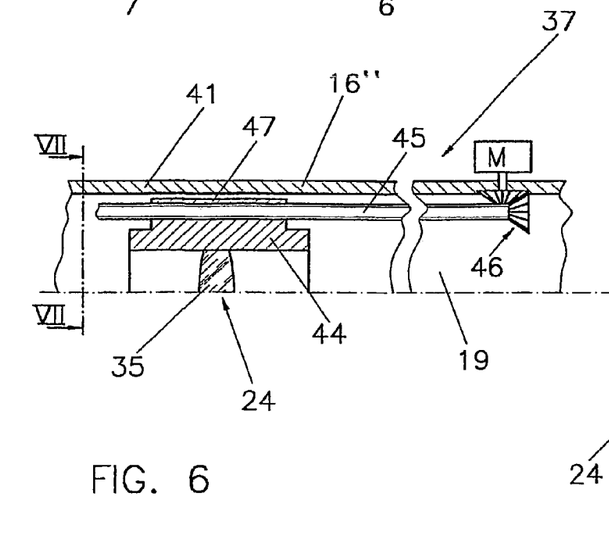
Figure 7:
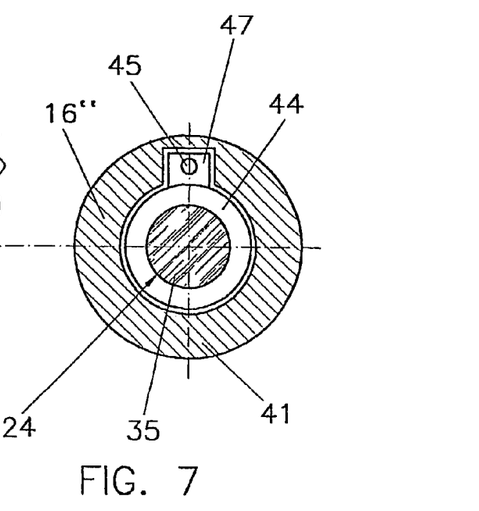
FIG. 7 shows a section along line VII—VII of FIG. 6.

FIGS. 6 and 7 illustrate a constructive solution for the longitudinal movement of a focusing device 24 within an arm part 16". Thereby, a pipe part 44 carrying the lenses 35 is moved by the aid of a threaded rod 45 that is driven electrically via a motor M or manually via a gear 46. The pipe part 44 exhibiting the lenses 35 is guided in the arm part 16" by means of a fit. On its outer surface, it has a nut 47 penetrated by the threaded rod 45.

Instead of moving the focusing device 34 along an arm part 16", the arm part 16" itself might be designed so as to be telescopic, whereby two pipes slidable into each other might also be moved by the aid of a threaded rod such as indicated in FIGS. 6 and 7.

Figure 8:
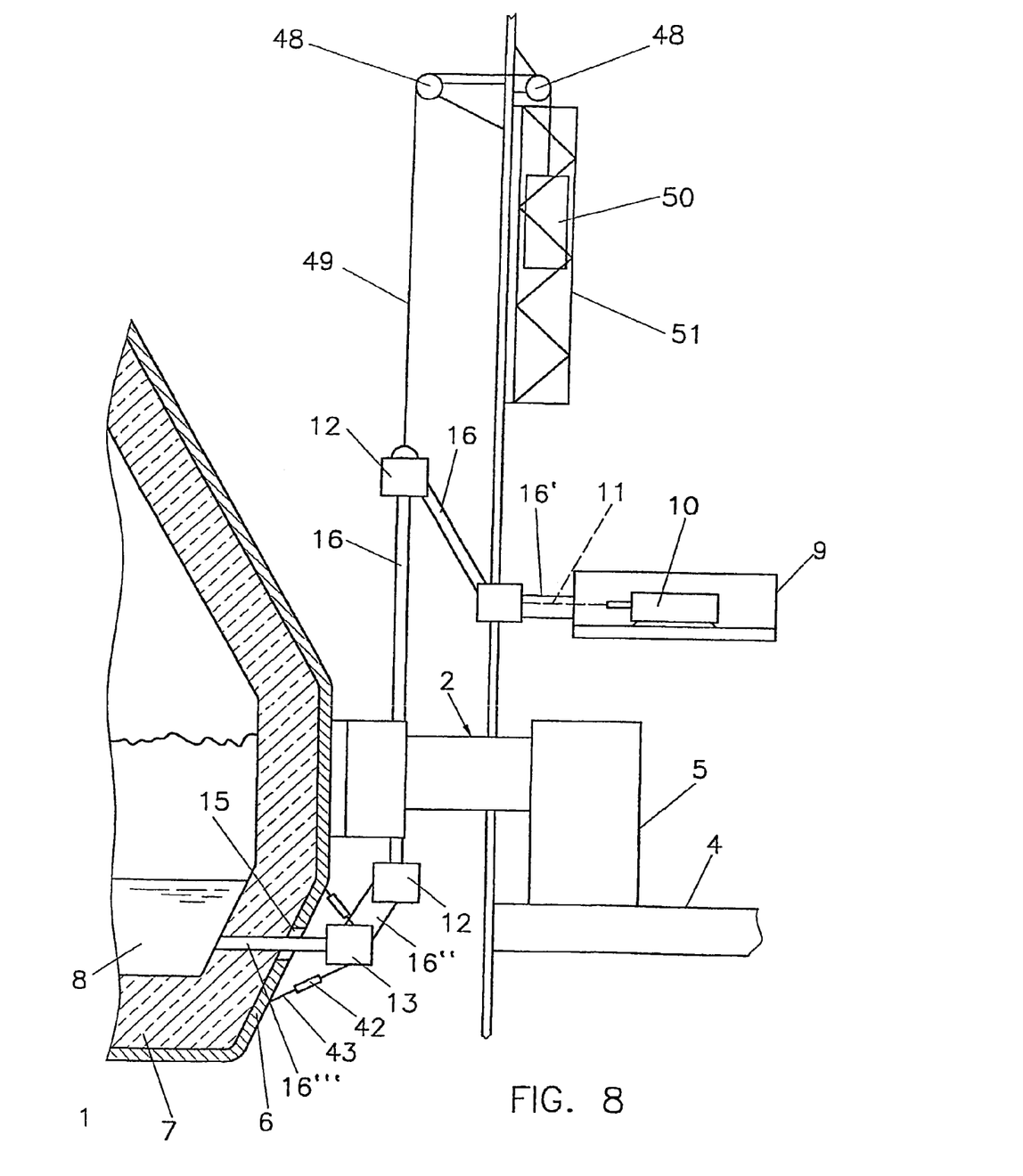
FIG. 8 illustrates an embodiment of the device according to the invention comprising a weight counterbalance, partially in section, partially in side view.

FIG. 8 illustrates a possible embodiment of a weight counterbalance for the arm 14. The latter is connected with a counterweight 50 by means of a rope 49 conducted over deflection rollers 48, which counterweight is guided so as to be movable along a guide or in a protective framing 51. According to FIG. 8, the arm 14 is not guided through the lifting lug 2 of a steelworks converter 1 but in parallel to the same outside the lifting lug 2. That brings about a somewhat restricted possibilty of movement, i.e. the steelworks converter 1 cannot be pivoted about the lifting lugs 2 by 360° but only by a smaller amount.

The invention is not limited to the exemplary embodiments illustrated in the drawing but may be modified in various respects. For example, it may be applied to any metallurgical vessel, i.e. also to electric furnaces and other melt-down aggregates such as melter gasifiers. In general, the device according to the invention can be used for any poorly accessible material sample 8, f.i., also for radioactive samples. It proves to be suitable, above all, for bridging over larger distances between the laser source 10 and the material samples and if space conditions are restricted.

What is claimed is:

1. A device for the chemical analysis of solid or molten material samples (8) present in a metallurgical vessel (1), based on the laser-induced emission spectroscopy, comprising a laser source (10) generating a laser beam (11), a deflection device (21) deflecting the laser beam, a focusing device (24) focusing the laser beam (11) as well as a device (14, 21, 27) that guides the reflections (26) of a plasma (25) ignited by the laser beam (11) on the material sample (8) to an evaluation device (28), characterized in that, between the laser source (10) and the material sample (8), an arm (14) equipped with at least one movable joint (12) and having a cavity (19) for the laser beam (11) is provided for guiding the laser beam (11), with the deflection device shaped as a mirror (21) or a prism being provided at the articulation thereof, and that the laser source (10) as well as the evaluation device (28) are arranged so as to be independent of the material sample (8) in terms of their movements and that the arm (14) is equipped with the deflecting device (21) for guiding the reflections (26) to the evaluation device (28).

2. A device according to claim 1, characterized in that the arm (14) is equipped with several movable joints (12) and optionally one or several rigid joint(s) (13) and deflection devices shaped as mirrors (21) and/or prisms are provided exclusively at the joints (12, 13) interconnected by arm parts (16, 16''), as well as optionally at the ends of the arm (14).

3. A device according to claim 1, characterized in that the evaluation device (28) comprises a spectrometer.

4. A device according to claim 1, characterized in that the evaluation device (28) is additionally equipped with a pyrometer for determining the temperature.

5. A device according to claim 1, characterized in that the evaluation device (28) is equipped with a device for taking photographic pictures.

6. A device according to claim 1, characterized in that the focusing device (24) is provided between the joint (12) arranged to be the penultimate one and the joint (13) arranged to be the last one before the material sample (8).

7. A device according to claim 1, characterized in that the focusing device (24) is provided between the last joint (13) before the material sample (8) and the material sample (8).

8. A device according to claim 1, characterized in that the focusing device (24) is movable in the longitudinal direction of the laser beam (11).

9. A device according to claim 8, characterized in that the movement of the focusing device (24) is controllable by the reflections (26) via an adjustment unit (37).

10. A device according to claim 1, characterized in that an arm part (16", 16''') arranged between two joints (12, 13) or between a joint (13) and the material sample (8) is telescopically extendable and contractable by means of a movable device in order to keep the distance between the focusing device (24) and the material sample (8) constant.

11. A device according to claim 1, characterized in that the arm (14) is provided with a heat protection.

12. A device according to claim 1, characterized in that the arm (14) is provided with a cooling device by means of which a cooling medium can be conducted through the arm.

13. A device according to claim 1, characterized in that the arm (14) is equipped with a device for measuring the temperature and a control circuit for minimizing any temperature differences within the arm (14).

14. A device according to claim 1, characterized in that the laser beam (11) and optionally the reflections (26) are guided so as to be rotationally symmetrical relative to the axis of rotation (18) of the movable joints (12), by means of the deflection devices shaped as mirrors (21) and/or prisms.

15. A device according to claim 14, characterized in that the deflection devices shaped as mirrors (21) are provided with reflective layers arranged in segments, with one reflective layer being provided for the laser beam (11) and another one for the reflections (26).

16. A device according to claim 1, characterized in that the focusing device (24) is equipped with segmented lenses and/or mirrors, with one segment being provided for the laser beam (11) and another one for the reflections (26).

17. A device according to claim 1, characterized in that the arm (14) is positioned in space in a moment-free fashion via a weight counterbalance, by means of a counterweight (50).

18. A metallurgical vessel (1) comprising a device for the chemical analysis of a melt (8), characterized by a device according to claim 1.

19. A metallurgical vessel according to claim 18, characterized in that the vessel (1) is tiltable and that an arm part (16') is arranged in parallel to the tilting axis or in the tilting axis.

20. A device according to claim 12, wherein the cooling medium is a liquid.

21. A device according to claim 12, wherein the cooling medium is a circulation gas.

22. A device according to claim 21, wherein the circulation gas is argon.

* * * * *